United States Patent [19]

Fontaine et al.

[11] Patent Number: 5,527,354

[45] Date of Patent: Jun. 18, 1996

[54] STENT FORMED OF HALF-ROUND WIRE

[75] Inventors: Arthur B. Fontaine, Fresno; Michael D. Dake, Stanford, both of Calif.

[73] Assignee: Cook Incorporated, Bloomington, Ind.

[21] Appl. No.: 216,782

[22] Filed: Mar. 22, 1994

Related U.S. Application Data

[63] Continuation of Ser. No. 929,150, Aug. 13, 1992, and Ser. No. 943,000, Sep. 10, 1992, abandoned, which is a continuation-in-part of Ser. No. 874,347, Apr. 24, 1992, abandoned, which is a continuation-in-part of Ser. No. 858,304, Mar. 25, 1992, abandoned, which is a continuation-in-part of Ser. No. 769,216, Oct. 1, 1991, Pat. No. 5,314,472, which is a continuation of Ser. No. 723,525, Jun. 28, 1991, Pat. No. Des. 539,802, said Ser. No. 929,150, is a continuation-in-part of Ser. No. 847,247, Mar. 9, 1992.

[51] Int. Cl.⁶ .............................. A61F 2/06; A61M 29/02
[52] U.S. Cl. ............................. 623/1; 623/12; 606/194; 606/195
[58] Field of Search .................. 623/1, 11, 12; 600/36; 606/191–193, 194–200, 151–158

[56] References Cited

U.S. PATENT DOCUMENTS

| | | | |
|---|---|---|---|
| 4,512,338 | 4/1985 | Balko et al. | 128/1 R |
| 4,553,545 | 11/1985 | Maass et al. . | |
| 4,580,568 | 4/1986 | Gianturco | 128/345 |
| 4,649,922 | 3/1987 | Wiktor | 128/344 |
| 4,655,771 | 4/1987 | Wallsten . | |
| 4,665,918 | 5/1987 | Garza et al. | 128/343 |
| 4,733,665 | 3/1988 | Palmaz . | |
| 4,739,762 | 4/1988 | Palmaz . | |
| 4,776,337 | 10/1988 | Palmaz . | |
| 4,787,899 | 11/1988 | Lazarus . | |
| 4,795,458 | 1/1989 | Regan . | |
| 4,800,882 | 1/1989 | Gianturco | 128/343 |
| 4,820,298 | 4/1989 | Leveen et al. | 623/1 |
| 4,830,003 | 5/1989 | Wolff et al. . | |
| 4,856,516 | 8/1989 | Hillstead . | |
| 4,878,906 | 11/1989 | Lindemann et al. . | |
| 4,886,062 | 12/1989 | Wiktor . | |
| 4,893,623 | 1/1990 | Rosenbluth | 606/192 |
| 4,922,905 | 5/1990 | Strecker . | |
| 4,950,227 | 8/1990 | Savin . | |
| 4,954,126 | 9/1990 | Wallsten . | |
| 4,969,458 | 11/1990 | Wiktor | 606/194 |
| 4,969,890 | 11/1990 | Sugita et al. . | |
| 5,015,253 | 5/1991 | MacGregor | 623/1 |
| 5,019,090 | 5/1991 | Pinchuk | 606/194 |
| 5,035,706 | 7/1991 | Gianturco | 606/198 |
| 5,041,126 | 8/1991 | Gianturco | 606/195 |
| 5,133,732 | 7/1992 | Wiktor | 606/195 |
| 5,135,536 | 8/1992 | Hillstead | 606/195 |

FOREIGN PATENT DOCUMENTS 183372 6/1986 European Pat. Off. ........ A61M 29/00

OTHER PUBLICATIONS

Atlantic Thermoplastics Co. Inc., James B. Sullivan & Richard Fox v. Faytex Corp., 974 F. 2nd 1279.
Atlantic Thermoplastics Co. Inc., James B. Sullivan & Richard Fox v. Faytex Corp. 974 F. 2nd 1299.
Atlantic Thermoplastics Co., Inc., James B. Sullivan & Richard Fox v. Faytex Corp. 970 F. 2nd 834.

Primary Examiner—Debra S. Brittingham
Attorney, Agent, or Firm—Richard J. Godlewski

[57] ABSTRACT

A vascular prosthesis stent provides an interior surface that reduces hemodynamic disturbances which interfere with blood flow through the stent and minimizes the reactive tissue response. More particularly, the vascular stent is constructed from a continuous wire that is half-round (i.e., semi-circular) in transverse cross-section. In a completed stent, the semi-circular wire profiles are all on the exterior of the stent body while the planar portions of the wire are all on the interior, with the result that the interior of the stent, comprised of the cross-sectional diameters of the wires, provides a generally smooth surface that minimizes blood flow turbulence, and minimizes the amount of tissue reaction necessary to incorporate the stent into the vessel wall.

16 Claims, 4 Drawing Sheets

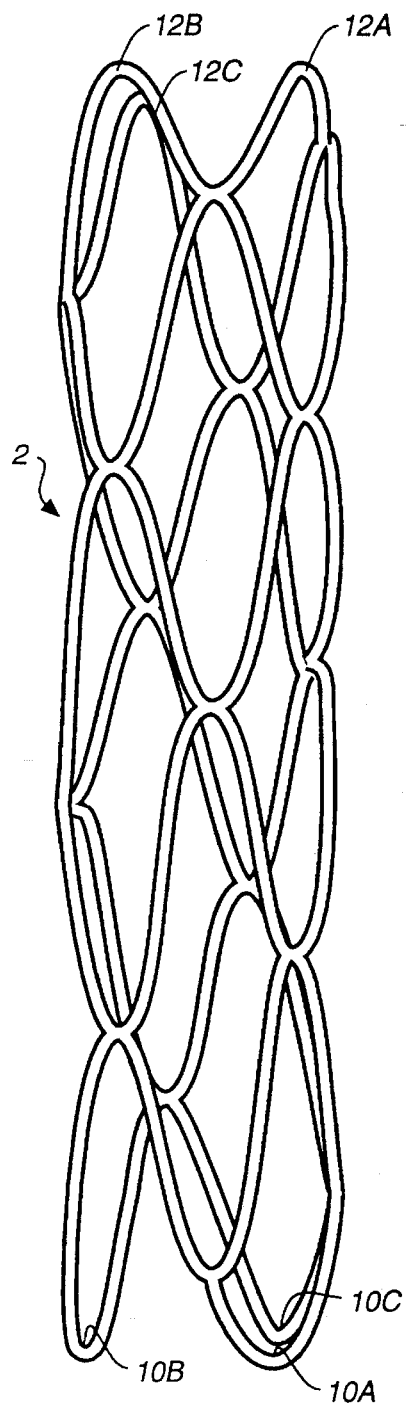
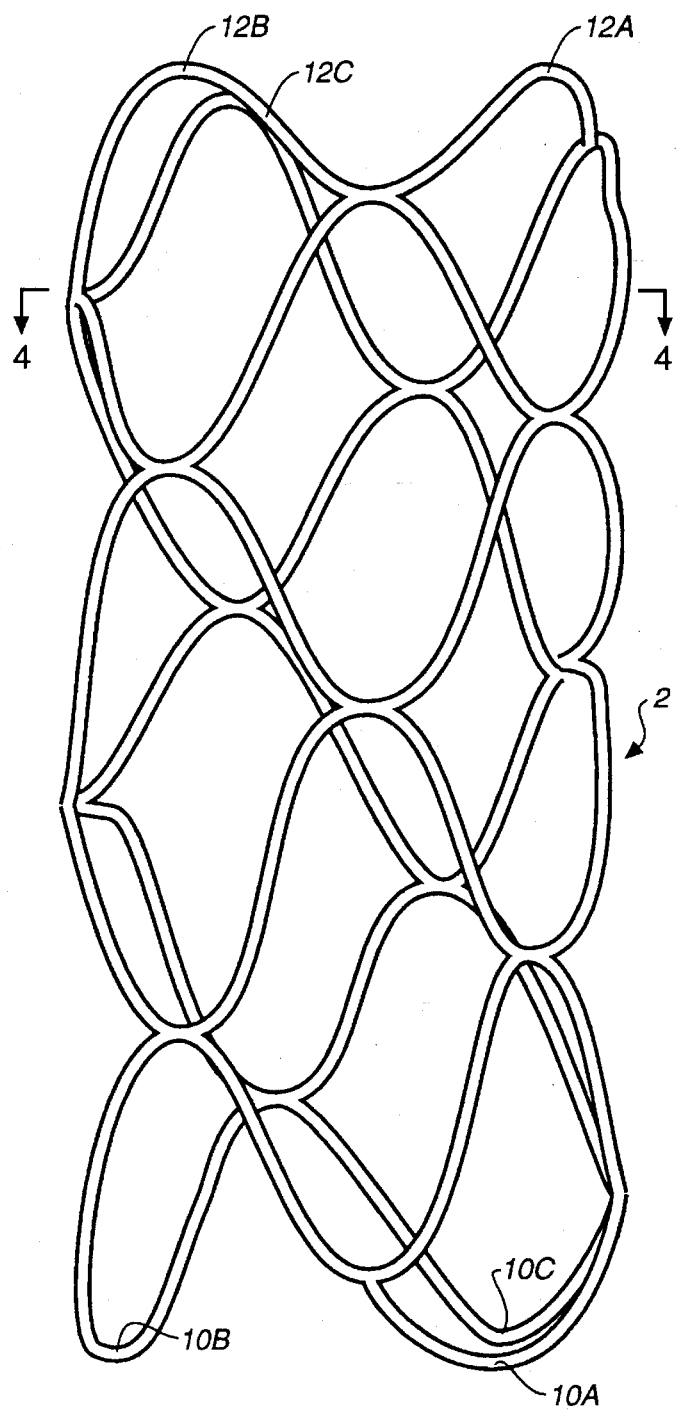
FIG._1
FIG._2

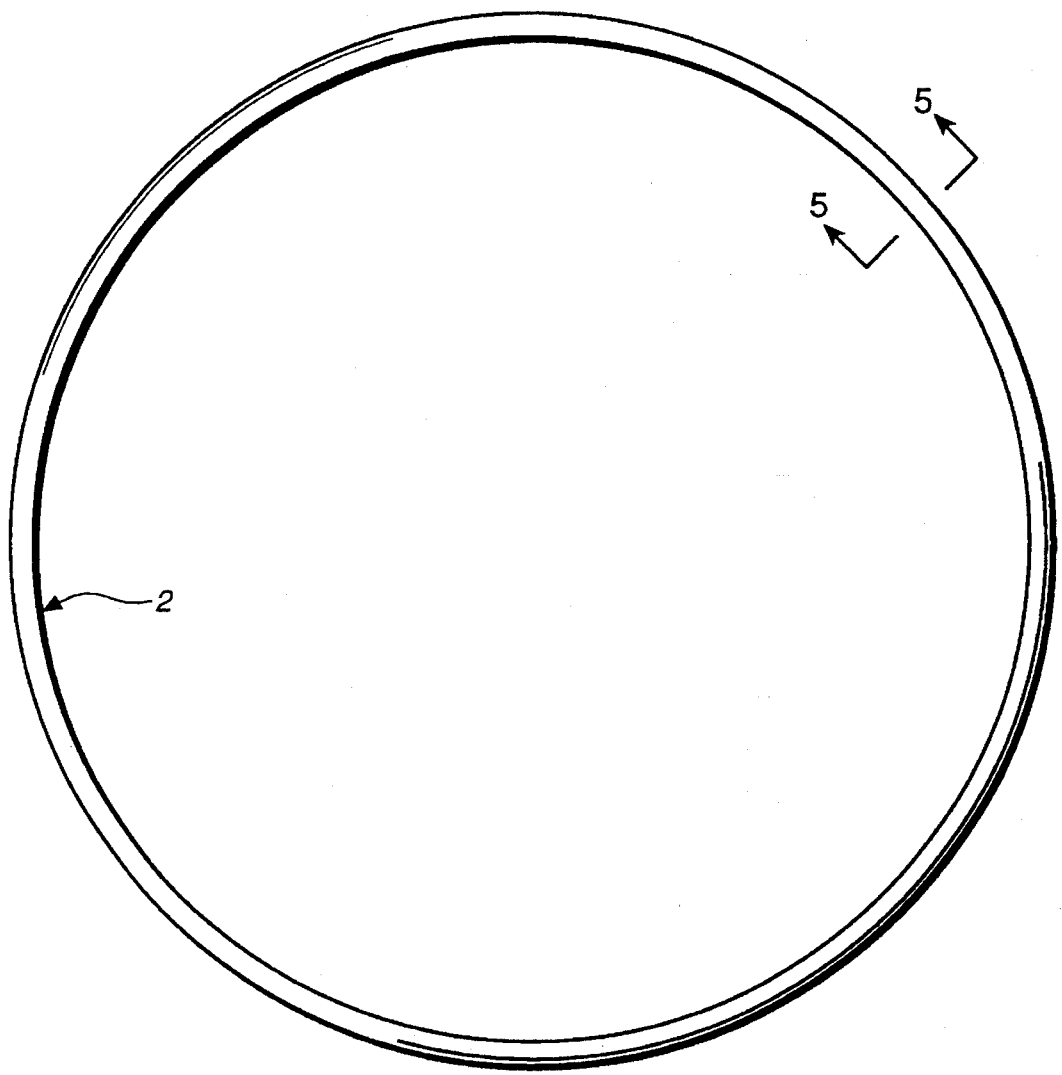
FIG._3
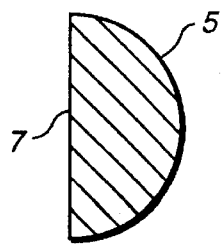
FIG._5

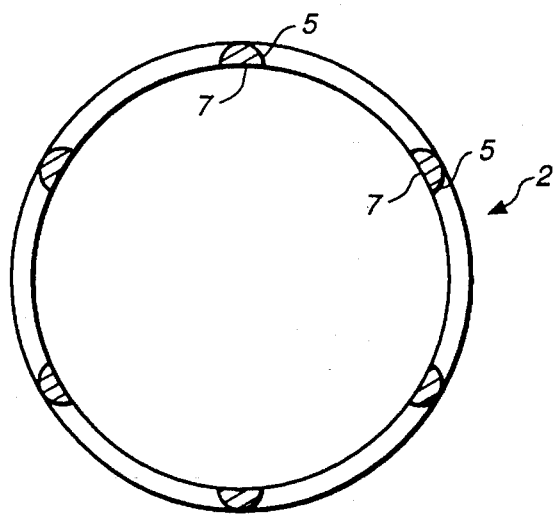
FIG._4
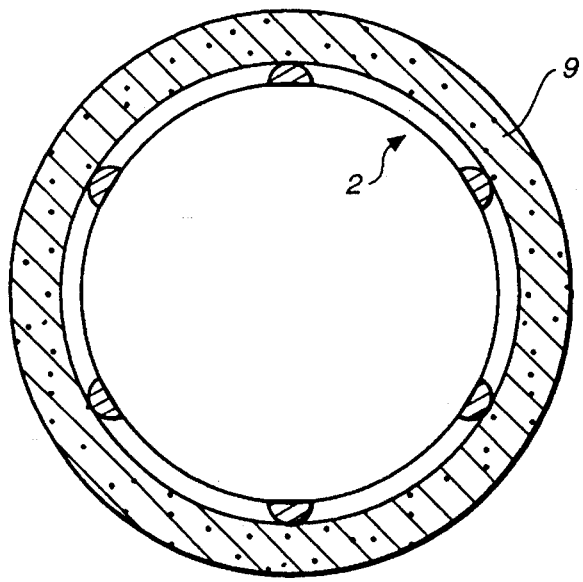
FIG._6A
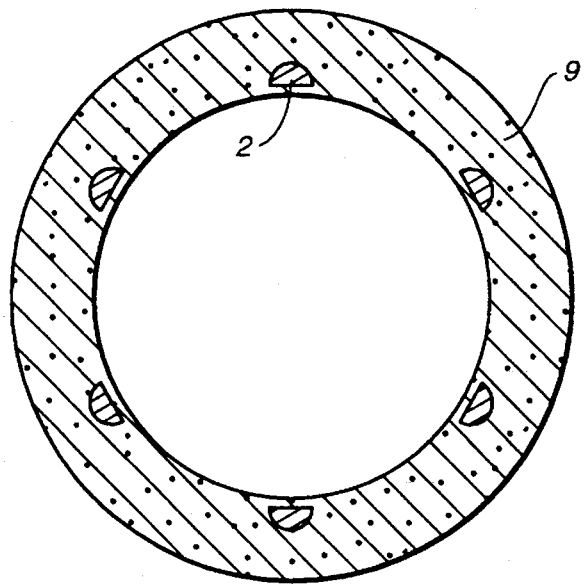
FIG._6B

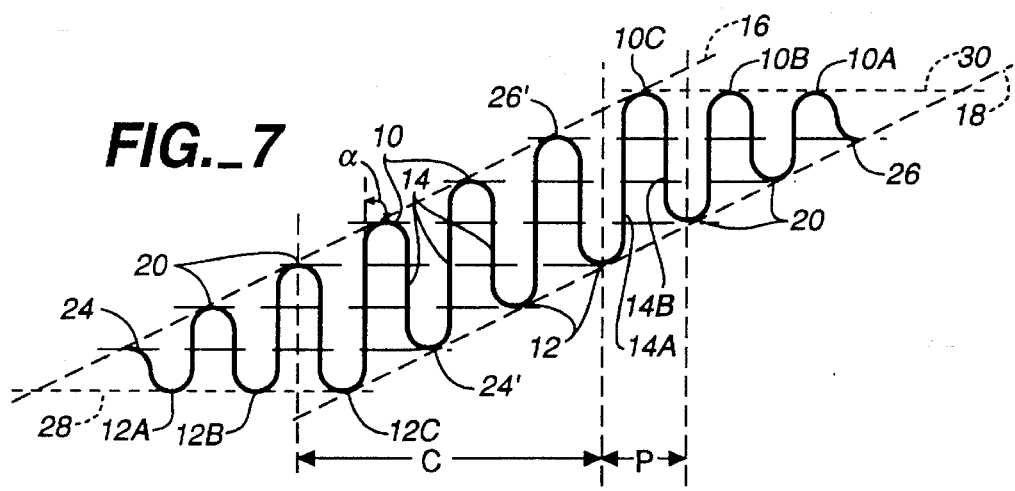
FIG._7
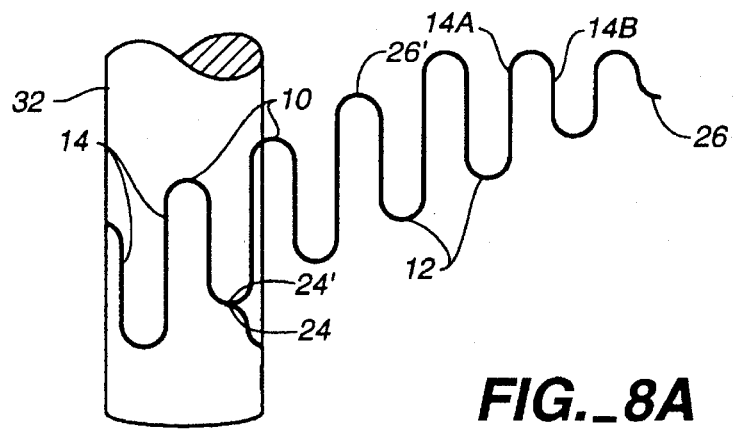
FIG._8A
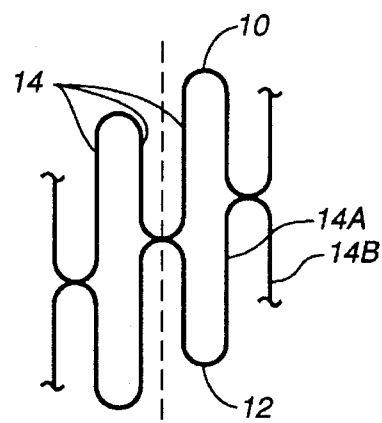
FIG._8B

STENT FORMED OF HALF-ROUND WIRE

This application is a continuation of Design patent application Ser. No. 07/929,150, still pending, filed Aug. 13, 1992, for Stent, which in turn is a continuation-in-part of Design patent application Ser. No. 07/847,247, still pending, filed Mar. 9, 1992, for Stent, which in turn is a continuation-in-part of Design patent application Ser. No. 07/723,525, now U.S. Pat. No. D539,802, filed Jun. 28, 1991, for Vascular Stent.

This application is also a continuation of Utility patent application Ser. No. 07/943,000, filed Sep. 10, 1992 now abandoned, which is a continuation-in-part of Utility patent application Ser. No. 07/874,347, now abandoned, filed Apr. 24, 1992, for a Vascular Stent and Method of Making and Implanting a Vascular Stent, the disclosure of which is incorporated herein in its entirety, which application in turn is a continuation-in-part of copending Utility patent application Ser. No. 07/858,304, now abandoned, filed Mar. 25, 1992, for Vascular Stent, which in turn is a continuation-in-part of Utility patent application Ser. No. 07/769,216, now U.S. Pat. No. 5,314,472 filed Oct. 1, 1991, for Vascular Stent, which in turn is a continuation of Design patent application Ser. No. 07/723,525 now U.S. Pat. No. D539,802 filed Jun. 28, 1991, for Vascular Stent.

All related applications listed above are commonly assigned herewith.

BACKGROUND OF THE INVENTION

1. Field of the Invention

The present invention relates to endoprothesis devices such as vascular stents and, more particularly, to vascular stents that are radially expandable.

2. State of the Art

Vascular stents are prosthetic devices that can be placed inside a lumen to support the lumen and to assure its patency. Stents are frequently implanted within vascular systems to reinforce collapsing, partially occluded, weakened, or abnormally dilated sections of blood vessels. Stents are widely used in angioplasty procedures which are concerned with the repair and reconstruction of blood vessels. More generally, however, stents can also be used inside the lumen of any physiological conduit including the arteries, veins, bile ducts, urinary tract, alimentary tract, tracheobronchial tree, cerebral aqueduct, and genitourinary system. Stents can also be used inside lumina of animals other than humans.

In one typical procedure for implanting a stent in a blood vessel, the stent is mounted on a balloon-tip catheter which is then slipped through an incision in the vessel wall and worked along the length of the vessel until a position is reached where the stent bridges a diseased or narrowed section of the vessel. Then the balloon on the balloon-tip catheter is inflated to radially expand the stent in place against the inside wall of the vessel while the vessel is dilated by the inflated balloon.

In practice, stents should be as atraumatic as possible to vessels and blood cells. As suggested by the above-identified application, one manner for reducing trauma is to form stents from biocompatible material and to minimize the quantity of material used. Trauma also can be reduced by devising stents that have exterior surfaces that are free from tines or sharp edges that might damage the wall of a blood vessel that surrounds the stent. Further trauma can be reduced by devising stents that, as again suggested by the above-identified application, have sufficient flexibility in their compressed state to conform to the tortuous paths of vessels through which the stent is inserted while being generally rigid in their expanded state.

SUMMARY OF THE INVENTION

Generally speaking, the present invention provides a vascular prosthesis stent having an interior configuration that reduces trauma. More particularly, the present invention provides a vascular prosthesis stent that provides an interior surface that reduces hemodynamic disturbances which interfere with blood flow through the stent.

In the preferred embodiment, a vascular prosthesis stent according to the present invention is constructed from a continuous wire that is half-round (i.e., semi-circular) in transverse cross-section. In other words, in transverse cross-section, the wire has a semi-circular side and a substantially planar side. In a completed stent, the semi-circular wire profiles are all on the exterior of the stent body while the planar portions of the wire are all on the interior. As a result, the interior of the stent—comprised of the cross-sectional diameters of the wires—provides a generally smooth surface that minimizes blood flow turbulence along the interior of the stent.

As compared to full-round wire stents, the stent of the present invention provides less topography or elevation of the stent in a vessel. This is important because the stent is a foreign body relative to the vessel and will elicit a tissue reaction that covers the stent and incorporates it into the vessel wall. In comparison to full-round wire stents, the stent of the present invention reduces the thickness of foreign material which projects into the lumen and is in contact with flowing blood. Because the stent of the present invention is generally flush with the vessel wall, it will incite a less exuberant, thinner layer of healing tissue to cover the prosthesis. This results in less compromise of the vessel lumen. Therefore, in comparison to full-round wire stents, the stent of the present invention will allow a larger luminal diameter than full-round wire stents and, therefore, provides a relatively larger internal flow diameter of blood flow through a vessel.

In its preferred embodiment, the vascular prosthesis stent of the present invention has a sufficiently low profile (i.e. external diameter) in its compressed state that the stent can be inserted through a relatively small aperture in a blood vessel wall, thereby minimizing bleeding and damage to the vessel. Also, the low profile allows the stent to be easily moved through narrow vessels.

Further in its preferred embodiment, the vascular prosthesis stent of the present invention has an compressed profile which is independent of its expansion ratio. In other words, the ultimate expanded diameter of the stent is not a function of its compressed profile and, therefore, one size stent can be used for lumens of a wide range of diameters.

Still further in its preferred embodiment, the vascular prosthesis stent of the present invention has substantial flexibility in its compressed state while being generally rigid and having a high hoop strength in its expanded state. The flexibility of the compressed stent is important, as mentioned above, for inserting the stent through tortuous lumens. The hoop strength is important for resisting the radial forces from the artery after the stent is in place. Also, with the stent being substantially rigid after it is expanded inside a vessel, movement of the stent against the vessel intima is reduced after the stent is implanted. The reduction in movement is important for reducing trauma and for promoting healing of the vessel.

Even further still, the vascular prosthesis stent of the present invention, in its preferred embodiment, has a tubularly-shaped body comprised of a plurality of oblong, open cells which are staggered around the circumference of the body such that when the stent is in its compressed condition, the long sides of each oblong cell are substantially parallel to the stent's longitudinal axis. The adjoining cells normally are bonded together at a point between adjacent parallel sides on a cell so that, when the stent is expanded, the adjacent sides of each cell extend at an oblique angle to the longitudinal axis of the stent.

BRIEF DESCRIPTION OF THE DRAWINGS

The present invention will now be further described with reference to the following figures wherein like elements are provided with the same reference numerals. It should be noted that he drawings show the invention to an enlarged scale for purposes of clarity. In the drawings:

FIG. 1 is a side elevational view of a stent according to the present invention in compressed condition;

FIG. 2 is a side elevational view of the stent of FIG. 1 in expanded condition;

FIG. 3 is an end view of the stent of FIG. 2;

FIG. 4 is a cross-sectional view which is taken along the plane of the line 4—4 in FIG. 2 for viewing in the direction of the arrows;

FIG. 5 is an enlarged cross-sectional detail, taken along the plane of the line 5—5 in FIG. 3 for viewing in the direction of the arrows;

FIGS. 6A and 6B are views that correspond in orientation to FIG. 4 and which schematically show the stent of FIG. 1 embedded in the lumen of a blood vessel;

FIG. 7 is a schematic illustration of a planar waveform of a continuous wire which is used to form the stent of FIGS. 1 and 2; and FIGS. 8A and 8B are illustration of the continuous waveform of FIG. 4 wrapped around the circumference of a mandrel for forming the stent in its compressed condition.

DESCRIPTION OF THE PREFERRED EMBODIMENTS

A vascular prosthesis stent, as shown in FIGS. 1 through 3, has a tubularly-shaped body 2 formed from a continuous wire or the like. The tubularly-shaped body preferably is comprised of a plurality of cells that are formed from the continuous wire, with each of the cells having a plurality of sides. The cell sides extend substantially parallel to the longitudinal axis of the tubularly-shaped body when it is compressed (FIG. 1), but extend obliquely to the longitudinal axis of the tubularly-shaped body when it is expanded (FIG. 2). The construction of the stent is further described below and in the above-identified applications, especially co-pending application Ser. No. 07/874,347 filed in the United States Patent and Trademark Office on Apr. 24, 1992, and commonly assigned herewith, the disclosure of which is also incorporated herein in its entirety.

As can be seen in FIG. 5, the continuous wire that forms the tubularly-shaped stent body is half-round (i.e., semi-circular) in transverse cross-section. In other words, in transverse cross-section, the wire has a semi-circular side 5 and a substantially planar side 7. The substantially planar side 7 generally corresponds to the diameter of the wire. In practice, the planar side is smooth and has a polished appearance.

From the following, it can be understood that it is important for the stent wire to have a substantially planar side, but it is not necessary that the remainder of the periphery of the wire be semi-circular. Indeed, the remainder of the periphery of the wire can have a variety of arcuate and non-arcuate shapes.

As can be seen in FIG. 4, the continuous wire is wound such that the semi-circular wire profiles 5 are all on the exterior of the tubularly-shaped stent body while the planar portions 7 are all on the interior of the stent. As compared to a full-round wire design, the orientation of the half-round wire is important so that the interior of the stent—comprised of the cross-sectional diameters of the wires—provides a generally smooth surface that minimizes blood flow turbulence along the interior of the stent and reduces the thickness of reactive tissue required to cover the prosthesis and incorporate it into the vessel wall.

In use of the above-described stent, the stent is maneuvered along a blood vessel until it reaches desired location, whereat the stent is expanded by a balloon catheter for lodging inside of a lumen. When so expanded, the semi-circular profiles of the wires on the exterior of the stent press into the vessel wall. In fact, as suggested by FIG. 6A, the stent may expand sufficiently that all of the semi-circular profiles on the exterior of the stent are embedded in a vessel wall 9 to the extent that the planar portions of the wire are substantially flush with the vessel wall. As a result, the interior of the lumen is generally smooth without impedance from the embedded stent.

There are several benefits to the stent of the configuration shown in FIG. 1. One benefit, as mentioned above, is that the stent offers a generally smooth surface that reduces turbulence on blood flowing along the lumina supported by the stent and encourages blood platelet aggregation. As a result, this configuration minimizes the traumatic effect of the stent on vessels and blood cells. Further, this configuration promotes healing of the vessel.

As compared to full-round wire stents, the stent of the present invention provides less topography, or elevation, of the stent in the vessel. This is important because the stent configuration allows its planar surface to be embedded in a manner substantially flush with the inner surface of the vessel wall. Consequently, the normal healing reaction of the vessel wall in response to the stent insertion is relatively thin and less exuberant than that required to incorporate a full-round wire design which projects further into the lumen from the vessel wall. As an example, FIG. 6B shows the vessel of FIG. 6A with tissue healed over the stent; typically, the tissue layer (intimal hyperplasia) is about 100 angstroms thick.

Also in comparison to full-round wire stents, the stent of the present invention requires less reactive tissue to incorporate the stent into the vessel wall. Again this is important because the neointimal layer will be completed faster when the reaction requires less reactive tissue. Finally in comparison to full-round wire stents, because the stent of the present invention elicits a thinner circumferential layer of tissue healing, it can yield a larger luminal diameter than full-round wire stents and, therefore, provides a larger internal flow diameter for blood flow.

FIG. 7 shows one preferred pattern or waveform of the wire that forms the stent of the present invention. As shown, this pattern comprises a series of alternating U-shaped waves having a period p, peaks 10, and valleys 12. In section C in FIG. 7, each U-shape wave includes an ascending side 14A and a descending side 14B.

As further shown in FIG. 7, the peaks 10 and valleys 12 are interconnected by substantially straight sections 14. The straight sections 14 are substantially parallel to each other and, for that reason, are depicted as straight vertical lines in the drawings. (The term "substantially parallel" is intended to encompass the configuration of the straight portions 14 in the compressed and expanded stent.) In practice, the peaks and valleys are generally semicircular in shape and arranged to intersect the straight portions 14 at the tangent of each curved peak or valley, with the result that there are no discontinuities in the wire.

The outermost portions of the peaks 10 and valleys 12 in the middle section of the waveform are aligned along parallel axes 16 and 18, respectively. The axes 16 and 18 form an acute angle a with respect to the straight portions 14. The angle a is preferably 45 degrees so that if distance between each straight section is one unit, then each U-shaped wave in the middle section has one leg that is three units long while the other leg is four units long as shown by the parallel horizontal reference lines in FIG. 7. Other relative dimensions and angles, however, can be used. A curved stent can also be formed by, for example, slightly increasing the length of every third wave and decreasing the length of a corresponding wave to form an arched configuration such that one side of the tubularly-shaped body is slightly longer than the opposite side.

As also shown in FIG. 7, two waves 20 of different amplitudes are formed at the opposite ends of the stent, and each has two sides of the same length. The end sections of the waveform include peaks 10A, 10B, and 10C at one end of the stent and valleys 12A, 12B, and 12C at the other end. The outer edges, or apexes, of those valleys are aligned along the axis 28 which is substantially perpendicular to the straight portions 14 (which are horizontal in FIG. 7). Similarly, the apexes of peaks 10A, 10B, 10C are aligned with an axis 30 which is also perpendicular to the straight portions 14 of the waves 20 but displaced from axis 30. The ends of the wire 24, 26 are preferably formed into half of a valley 12 at one end and half of a peak 10 at the other end. The ends 26 may also include a small, straight portion (not shown) which may be parallel or perpendicular to the straight portions 14.

As shown in FIGS. 8A and 8B and as further described in the above-identified co-pending applications, the stent can be formed by wrapping wire formed in the waveform of FIG. 7 around a mandrel 32. Thus, these drawings show the tubularly-shaped body of the stent in its compressed condition. In practice, the circumference of the mandrel 32 corresponds to the dimension c, with the result that the peak 10 of one wave coincides with the valley 12 of another wave when the waveform is wrapped around a mandrel with straight portions 14 aligned with the longitudinal, or central, axis of the mandrel to produce multiple and symmetrical tangent points. As the wire is wrapped on the mandrel, some or all of the successive junctions between the peaks 10 and valleys 12 are bonded to one another to form bonded cells until the stent is complete as shown in the drawings. The flexibility of the stent can be controlled by bonding fewer than all of the peaks 10 to corresponding valleys 11.

The formation of the stent about the mandrel in the preferred embodiment can be summarized by observing that the continuous wire is formed into an asymmetric undulating wave pattern around the circumference of the tubularly-shaped stent body with each wave having a long ascending side and a short descending side, with a peak between the long ascending side and the short descending side and a valley between the short descending side and a long ascending side of an adjacent wave, and the ascending and descending sides of each wave being arranged substantially parallel to the longitudinal axis of the body when the body is in a compressed condition. Further, as the continuous wire is wound around the cylindrical mandrel, the wire configuration is adjusted so that the $n^{th}$ peak comes into tangency with the valley immediately following peak $n^{th}+3$, and so forth so that all peaks and valleys are in tangency. Then pairs of the tangent points are fixed together by means of a weld to form a plurality of cells arranged substantially parallel to the long axis of the mandrel. Preferably, the long side of the wave and the short side of the wave are in a ratio of about 4:3. Also, as mentioned above, at least some of the peaks and valleys of the waves are bonded together to form a plurality of cells.

It should be particularly noted the waveform is wrapped around the mandrel 32 so that the planar face of the half-round wire is in contact with the mandrel. That is, the mandrel surface is tangent to the substantially planar face of the half-round wire and the semi-circular surface of the half-round wire faces outward from the mandrel. Thus, when the tubularly-shaped stent is removed from the mandrel, it is in the compressed condition shown in FIG. 1.

It should also be noted that the end 24 of the waveform is wrapped around the mandrel 32 so it is tangent to point 24'. Similarly, end 26 is tangent to point 26' when the wave is completely wrapped around the mandrel 32. In practice, the ends 24, 26 are bonded (as by welding, brazing, soldering, tying, looping, adhesive bonding, or other suitable means) so that the ends of the wire are not exposed to snag or otherwise interfere with the placement of the stent in the vessel.

The planar waveform is compressed perpendicular to straight sections 14 to form an undulating pattern before being wrapped around the mandrel 32. In these conditions, the straight portions 14 are substantially parallel to longitudinal axis of the tubularly-shaped stent body.

The stent of the present invention expands radially when subjected to the internal radial pressure of an expanding catheter balloon. The peaks 10 and valleys 12 between the waves operate like flexible junctions, or hinges, and allow the straight portions 14 to move outwardly in directions oblique to the central axis of the stent body. However, after the stent is expanded, the junctions resist displacement of the straight sections in the opposite direction (for example, due to the compressive force of the lumen) which would tend to reduce the diameter of the expanded stent. The resistance of these junctions to compression is a measure of the hoop strength of the stent.

FIG. 7 shows a waveform wherein the period (or wavelength) of each wave p is roughly one-fourth of the mandrel circumference c. In practice, this configuration reduces the number of waves, the number of bonds between waves, and amount of wire required to adequately support the lumen. In the illustrated embodiments, the end of the stent has three peaks 10A, 10B, and 10C, and three valleys 12A, 12B, and 12C exposed on the end of the expanded stent as shown in FIG. 2. The apex of peaks and valleys are equally spaced at 120, 240, and 360 degrees, respectively, around the end face of the stent. This preferred configuration provides the maximum lumen support and minimum profile (i.e. diameter) in the compressed condition using the least possible amount of foreign material inside the body. Conventional stents have been found to use more than three peaks or valleys around the end circumference of the body which increases their compressed profile and uses more material than is necessary.

When the stent is properly expanded, each apex of peaks 10A–10C and valleys 12A–12C moves in the radial direction away from the longitudinal axis of the tubularly-shaped body of the stent. Consequently, the stent does not migrate inside a lumen during expansion.

Referring again to FIG. 1, it can be seen that the side profile of the stent in its expanded state is defined by cells that have generally rhombic shapes with four sides. As mentioned above, the wire is bonded at the tangent points between adjacent sides to form bonded cells. The above-discussed straight portions 14 extend obliquely to the central axis of the tubularly-shaped body when the stent is expanded as shown in FIG. 2.

In practice, the expansion ratio of the stent can be adjusted by changing the height of the waves (as defined by the distance between axis 16 and axis 18.) It should be noted that increasing the length of straight sections 14 increases the ultimate expansion ratio of the stent without affecting its compressed diameter. Consequently, the ultimate expanded diameter of the stent is independent of its compressed diameter so that one size stent can be used with almost any size lumen. Moreover, even large lumens can be supported with a stent that has a small compressed profile so that bleeding and vessel damage is reduced during implantation. In practice, the stent has been found to work well with expansion ratios of between 1:1 and 10:1; however, larger expansion ratios are also possible. The ultimate expansion ratio can also be increased by decreasing the period of the waves p and/or the distance between straight sections 14 so that more waves are created around the circumference of the stent.

The above-described stent has a wide variety of uses. For example, the stent can be used inside a graft for repairing a pseudo-aneurysm in a common femoral artery. In such use, the stent may be located completely inside a graft or may extend outside the edges of the graft to provide additional support for the incisions at the end of the graft. Also, two or more of the above-identified stents may be used at each end of a graft for bypassing an occlusion in, for example, a femoral-popliteal artery. Still further, two or more of the above-identified stents may be used with a branched graft to repair an aorta-iliac aneurysm.

In operation, the compressed stent is mounted on a catheter for insertion into a lumen. Then, during implantation, the compressed stent 2 and a catheter balloon are withdrawn inside the sheath onto the catheter while the sheath is slid inside a vessel lumen. Then, after the compressed stent 2 is moved to its appropriate position, the sheath is partially withdrawn so that the compressed stent 2 and the balloon are exposed inside the lumen. The balloon is then inflated and the stent 2 is expanded inside the lumen. Finally, the balloon is deflated and the catheter is removed from the lumen without the stent.

The stent material preferably has "low memory," which is to say that it does not try to resume its original shape after its is deformed. This is important for preventing the stent from recoiling to its compressed condition after implantation. In one preferred embodiment, the stent is formed from about 0.006 to 0.020 inch diameter annealed tantalum wire. The stent material may also be radio-opaque to allow its location in a vessel to be verified through fluoroscopic examination. Preferably, the stent is made from a biocompatible material (such as stainless steel) or a bio-absorbable material (such as Vicryl). The stent may also be coated with anti-thrombolytic or anti-coagulant agents such as Dextran, Heperin, t-PA, polytetrafluoroethylene, or ultra low-temperature isotropic carbon.

The foregoing has described the principles, preferred embodiments and modes of operation of the present invention. However, the invention should not be construed as limited to the particular embodiments discussed. Instead, the above-described embodiments should be regarded as illustrative rather than restrictive. For example, as mentioned above, it is important for the stent wire to have a substantially planar side, but the remainder of the periphery of the wire can have a variety of arcuate and non-arcuate shapes. Accordingly, it should be appreciated that variations may be made in those embodiments by workers skilled in the art without departing from the scope of present invention as defined by the following claims.

What is claimed is:

1. A vascular prosthesis stent, comprising:

a continuous wire formed into an undulating wave pattern having a plurality of segments joined by a plurality of bends, said pattern being formed into a substantially tubularly-shaped body having a compressed and an expanded condition and a longitudinal axis, a plurality of bonded cells, each of the bonded cells having a plurality of sides and being formed from selected of said segments and said bends bonded together in abutting contact; and the continuous wire having a substantially semi-circular side and a substantially planar side, whereby an axial length of said tubularly-shaped body remains substantially equivalent in the expanded and the compressed conditions.

2. A vascular prosthesis stent according to claim 1 wherein the continuous wire is half-round in cross-sectional shape.

3. A vascular prosthesis stent according to claim 2 wherein the semi-circular side of the wire is on all exterior of the stent body and the planar side of the wire is on an interior of the stent body.

4. A vascular prosthesis stent according to claim 3 wherein the interior of the stent is smooth for providing a surface that minimizes blood flow turbulence along the interior of the stent.

5. A vascular prosthesis stent according to claim 1, formed from a continuous wire, wherein the bonded cells have sides that extend substantially parallel to a longitudinal axis of the tubularly-shaped body when the tubularly-shaped body is compressed and which extend obliquely to the longitudinal axis when the tubularly-shaped body is radially expanded.

6. A vascular prosthesis stent according to claim 5, wherein the bonded cells are oblong in geometric configuration when compressed and rhomboid in geometric configuration when expanded.

7. A vascular prosthesis stent according to claim 1, formed from a continuous wire, wherein at least one of the cells is bonded to an adjacent cell at a position between two adjacent sides of each of the cells.

8. A vascular prosthesis stent according to claim 1, formed from a continuous wire, wherein the cells have an oblong shape with a long axis of the oblong shape extending substantially parallel to the longitudinal axis of the tubularly-shaped body.

9. A vascular prosthesis stent according to claim 8, wherein the cells have sides that extend substantially parallel to the longitudinal axis of the tubularly-shaped body for, thereby, minimizing a diameter of the tubularly-shaped body in a compressed configuration.

10. A vascular prosthesis stent according to claim 8, wherein the cells have sides that extend substantially parallel to the longitudinal axis of the tubularly-shaped body for maximizing an expansion ratio of the tubularly-shaped body.

11. A vascular prosthesis stent according to claim 1, formed from a continuous wire, wherein the cells have four sides and are rhomboid in shape when the tubularly-shaped body is expanded.

12. A vascular prosthesis stent, comprising:

a continuous wire formed into an undulating wave pattern and a substantially tubularly-shaped body with a longitudinal axis and two ends, selected portions of said continuous wire being bonded together in abutting contact, the body having a compressed condition and an expanded condition; and the continuous wire being half-round in cross-sectional shape with a substantially semi-circular side and a substantially planar side, the semi-circular side of the wire being on an exterior of the stent body, the planar side of the wire being on an interior of the stent body, whereby an axial length of the tubularly-shaped body remains substantially equivalent in the compressed and the expanded conditions.

13. A vascular prosthesis stent according to claim 12, wherein the interior of the stent is smooth for providing a surface that minimizes blood flow turbulence along the interior of the stent.

14. A vascular prosthesis stent according to claim 12, wherein each wave has a long ascending side and a short descending side, with a peak between the long ascending side and the short descending side and a valley between the short descending side and a long ascending side of an adjacent wave and wherein the ascending and descending sides of each wave is arranged substantially parallel to the longitudinal axis of the body when the body is in the compressed condition.

15. A vascular prosthesis stent according to claim 14, in which the long side of the wave and the short side of the wave are in a ratio of about 4:3.

16. A vascular prosthesis stent according to claim 14, wherein at least some of the peaks and valley of the waves are bonded together to form a plurality of cells.

\* \* \* \* \*